(12) United States Patent
Matsuno et al.

(10) Patent No.: US 9,375,143 B2
(45) Date of Patent: Jun. 28, 2016

(54) ELECTRONIC APPARATUS AND COMMUNICATION CONTROL METHOD

(71) Applicant: KABUSHIKI KAISHA TOSHIBA, Minato-ku, Tokyo (JP)

(72) Inventors: Takaya Matsuno, Kunitachi (JP); Shingo Suzuki, Sagamihara (JP); Yusaku Kikugawa, Ome (JP); Koji Yamamoto, Ome (JP); Kentaro Takeda, Tokyo (JP); Takashi Sudo, Fuchu (JP); Tadashi Amada, Ome (JP); Yasuhiro Kanishima, Tokyo (JP); Chikashi Sugiura, Hamura (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 233 days.

(21) Appl. No.: 14/073,633

(22) Filed: Nov. 6, 2013

(65) Prior Publication Data

US 2014/0320307 A1    Oct. 30, 2014

(30) Foreign Application Priority Data

Apr. 26, 2013    (JP) .................................. 2013-094360

(51) Int. Cl.
   *A61B 5/00*       (2006.01)
   *G06F 19/00*      (2011.01)
   *A61B 5/11*       (2006.01)

(52) U.S. Cl.
   CPC .............. *A61B 5/0002* (2013.01); *A61B 5/002* (2013.01); *A61B 5/0022* (2013.01); *A61B 5/6802* (2013.01); *A61B 5/72* (2013.01); *A61B 5/742* (2013.01); *G06F 19/3418* (2013.01); *A61B 5/1112* (2013.01); *A61B 2560/0209* (2013.01); *A61B 2562/06* (2013.01); *G06F 19/345* (2013.01)

(58) Field of Classification Search
   CPC ............... A61B 5/002; A61B 5/0002–5/0022; A61B 5/72; A61B 5/742; A61B 5/68; A61B 5/6801–5/6802; A61B 5/7282; A61B 5/7285; G06F 19/3418; H04L 63/0861
   See application file for complete search history.

(56) References Cited

U.S. PATENT DOCUMENTS

| | | | |
|---|---|---|---|
| 2004/0155790 A1* | 8/2004 | Tsuji | 340/825.21 |
| 2007/0087790 A1* | 4/2007 | Worick et al. | 455/567 |
| 2007/0192032 A1* | 8/2007 | David et al. | 702/19 |
| 2008/0076978 A1 | 3/2008 | Ouchi et al. | |
| 2008/0088434 A1* | 4/2008 | Frieder et al. | 340/539.11 |
| 2008/0129465 A1* | 6/2008 | Rao | 340/286.02 |

(Continued)

FOREIGN PATENT DOCUMENTS

| | | |
|---|---|---|
| JP | 2006-170751 A | 6/2006 |
| JP | 2008-073456 A | 4/2008 |

(Continued)

*Primary Examiner* — Hai Phan
*Assistant Examiner* — Orlando Bousono
(74) *Attorney, Agent, or Firm* — Knobbe, Martens, Olson & Bear LLP

(57) ABSTRACT

According to one embodiment, an electronic apparatus includes a biological sensor, an extraction module, a state detector, and a transmission controller. The biological sensor generates first biological data. The extraction module extracts one or more first features from the first biological data. The state detector detects a communication state between a communication module and a server. The transmission controller transmits at least one of the first biological data and the one or more first features to the server, based on the detected communication state.

11 Claims, 8 Drawing Sheets

(56) References Cited

U.S. PATENT DOCUMENTS

| | | | |
|---|---|---|---|
| 2009/0007596 A1* | 1/2009 | Goldstein et al. | 63/1.11 |
| 2009/0216344 A1* | 8/2009 | Bretin | 700/21 |
| 2010/0160744 A1* | 6/2010 | Ha et al. | 600/301 |
| 2010/0190441 A1* | 7/2010 | Okuda et al. | 455/41.2 |
| 2010/0305414 A1* | 12/2010 | Koo et al. | 600/301 |
| 2011/0050392 A1* | 3/2011 | Kaizu | 340/5.52 |
| 2011/0221595 A1* | 9/2011 | Koraichi et al. | 340/573.1 |
| 2012/0050047 A1* | 3/2012 | Kim et al. | 340/573.1 |
| 2012/0184822 A1* | 7/2012 | Kim et al. | 600/300 |
| 2012/0293324 A1* | 11/2012 | Rao et al. | 340/539.12 |
| 2012/0313760 A1* | 12/2012 | Okano | 340/10.1 |
| 2013/0072770 A1* | 3/2013 | Rao et al. | 600/323 |
| 2013/0173461 A1* | 7/2013 | Levy | 705/39 |
| 2013/0300559 A1* | 11/2013 | Chien et al. | 340/539.12 |
| 2014/0320307 A1 | 10/2014 | Matsuno et al. | |

FOREIGN PATENT DOCUMENTS

| | | |
|---|---|---|
| JP | 2011-197565 A | 10/2011 |
| JP | 2014-213071 A | 11/2014 |

\* cited by examiner

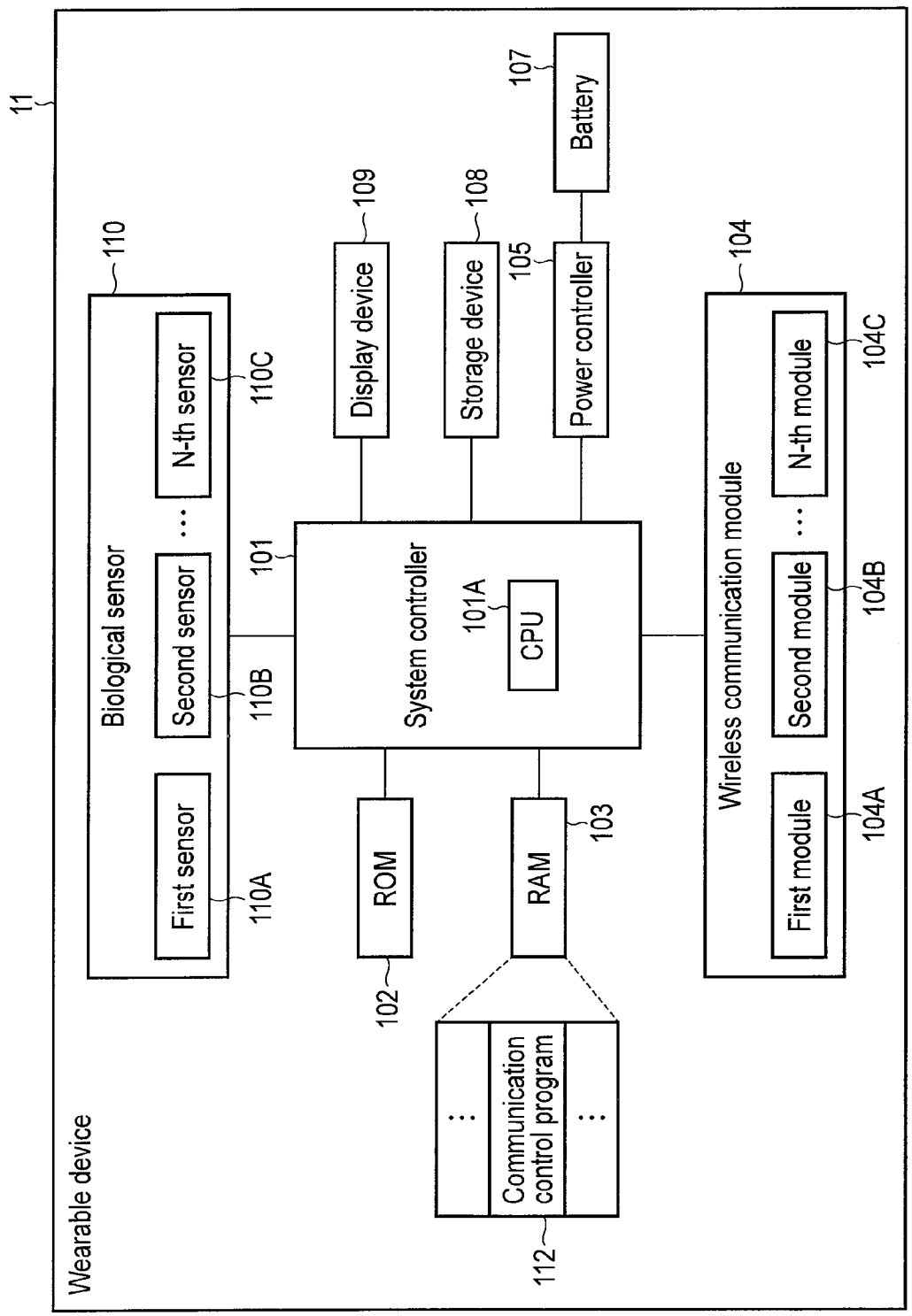
F I G. 2

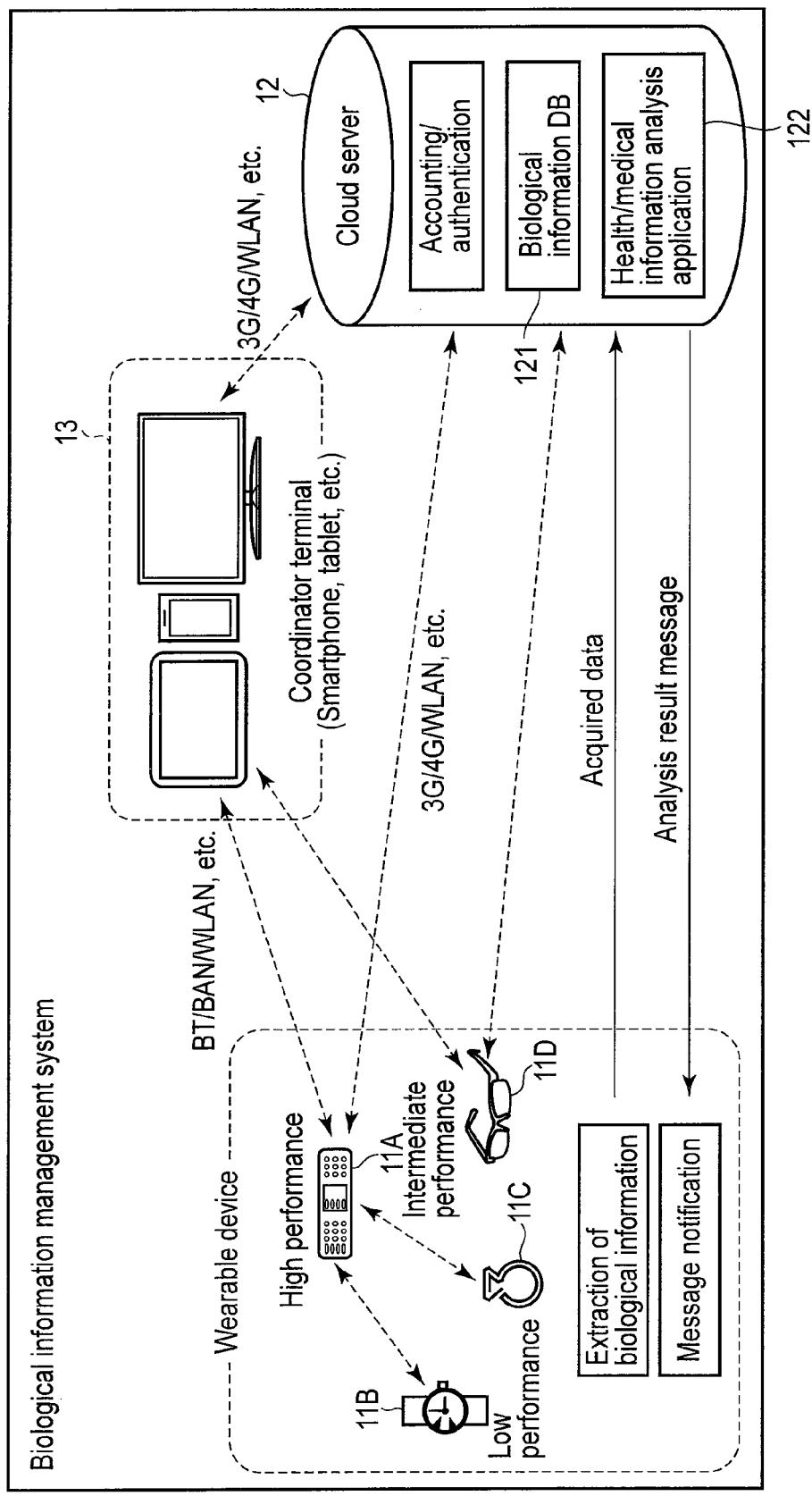
F I G. 4

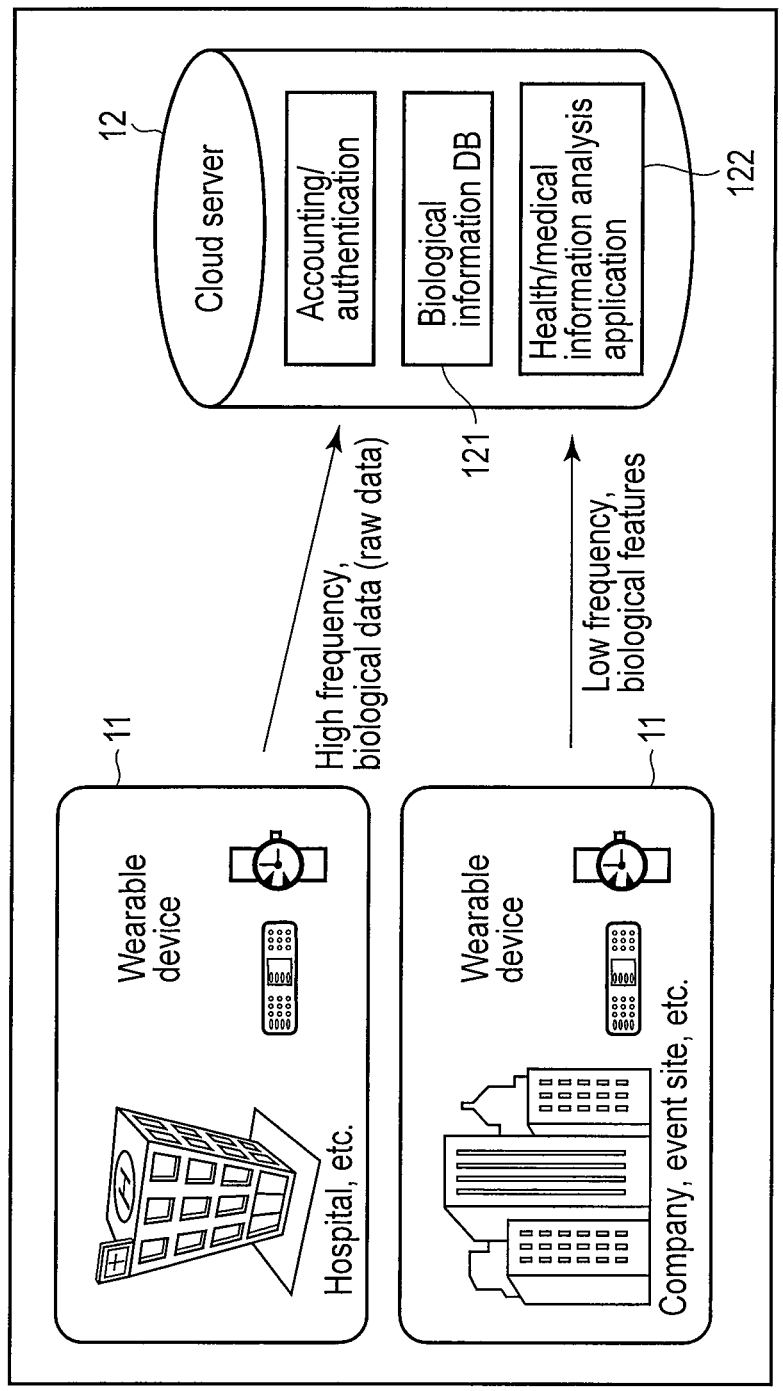
F I G. 5

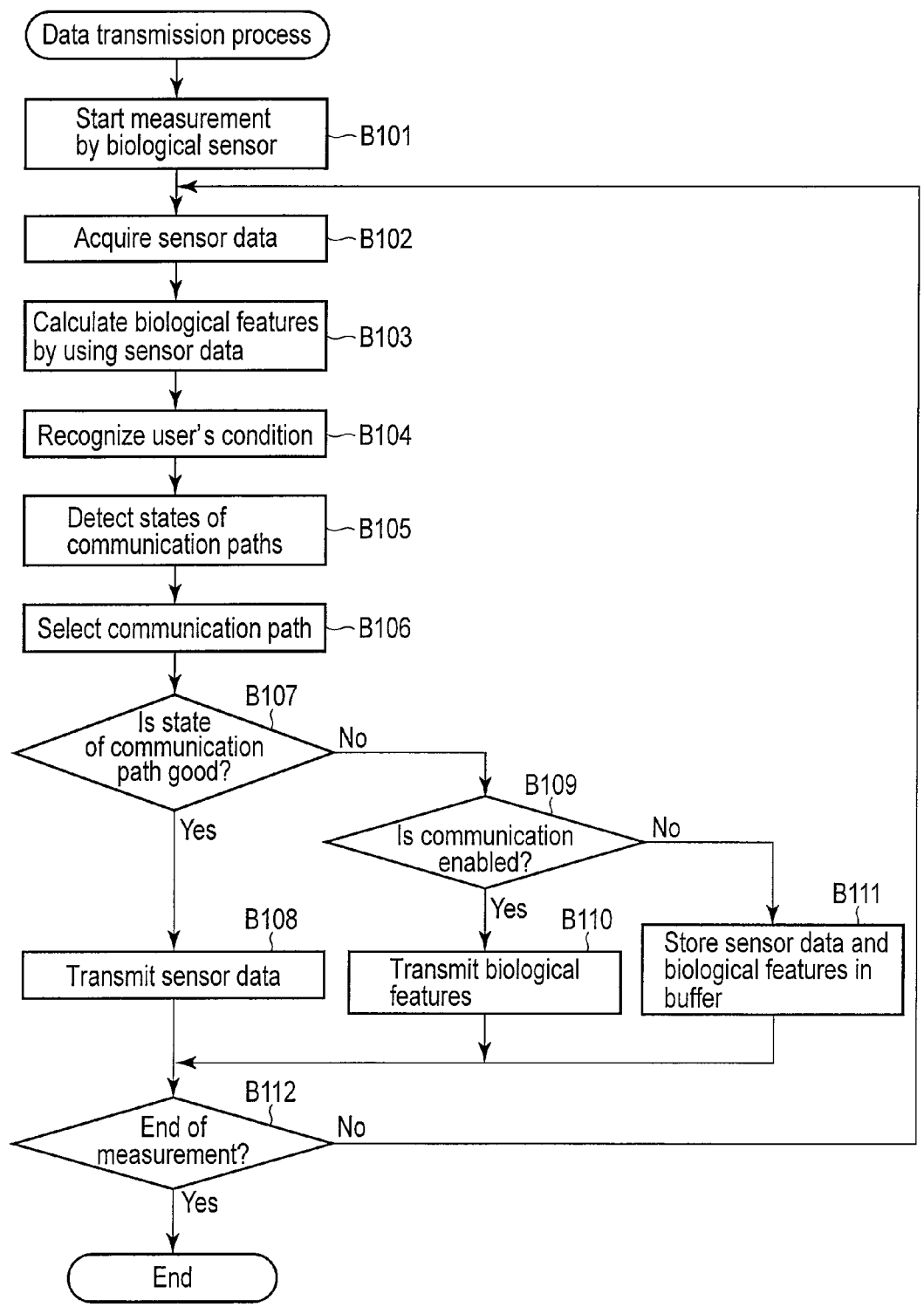
F I G. 6

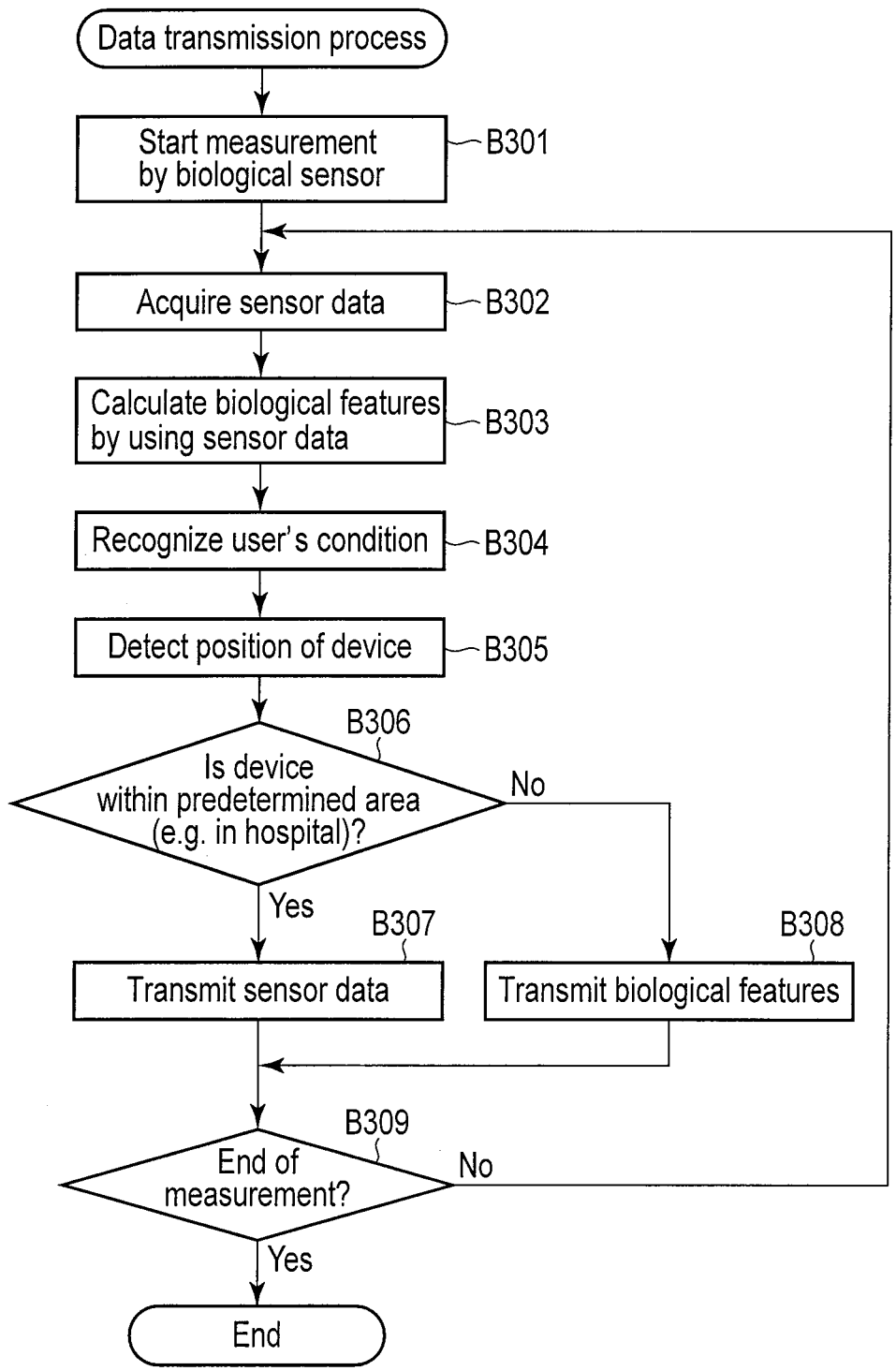
F I G. 8

ELECTRONIC APPARATUS AND COMMUNICATION CONTROL METHOD

CROSS-REFERENCE TO RELATED APPLICATIONS

This application is based upon and claims the benefit of priority from Japanese Patent Application No. 2013-094360, filed Apr. 26, 2013, the entire contents of which are incorporated herein by reference.

FIELD

Embodiments described herein relate generally to an electronic apparatus and a communication control method applied to this electronic apparatus.

BACKGROUND

In recent years, electronic apparatuses called "wearable devices", which users can wear (put on), have been gaining in popularity. The wearable device has a shape of, for example, a watch, glasses, a ring, a bracelet, a necklace, or a sticking plaster. The user can obtain various kinds of information by a display or a speaker which is provided on a wearable device that the user wears.

In some cases, such a wearable device is equipped with a biological sensor for acquiring the user's biological information. The biological sensor can detect biological information such as the user's pulse, ECG (electrocardiogram), or body temperature.

In the meantime, in some cases, the detected biological information is not only stored, but is also transmitted to a server over a network. Since the wearable device is driven by a battery, efficient transmission of biological information may possibly be required in order to suppress power consumption.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 2 is a block diagram illustrating an example of the system configuration of the electronic apparatus of the embodiment.

FIG. 4 is a view for describing another example of the biological information management system of FIG. 1.

FIG. 5 is a view for describing an example of biological information transfer according to locations where the electronic apparatus of the embodiment is used.

FIG. 6 is a flowchart illustrating an example of the procedure of a data transmission process executed by the electronic apparatus of the embodiment.

FIG. 8 is a flowchart illustrating still another example of the procedure of the data transmission process executed by the electronic apparatus of the embodiment.

DETAILED DESCRIPTION

Various embodiments will be described hereinafter with reference to the accompanying drawings.

In general, according to one embodiment, an electronic apparatus includes a biological sensor, an extraction module, a state detector, and a transmission controller. The biological sensor is configured to generate first biological data. The extraction module is configured to extract one or more first features from the first biological data. The state detector is configured to detect a communication state between a communication module and a server. The transmission controller is configured to transmit at least one of the first biological data and the one or more first features to the server, based on the detected communication state.

Figure 1:
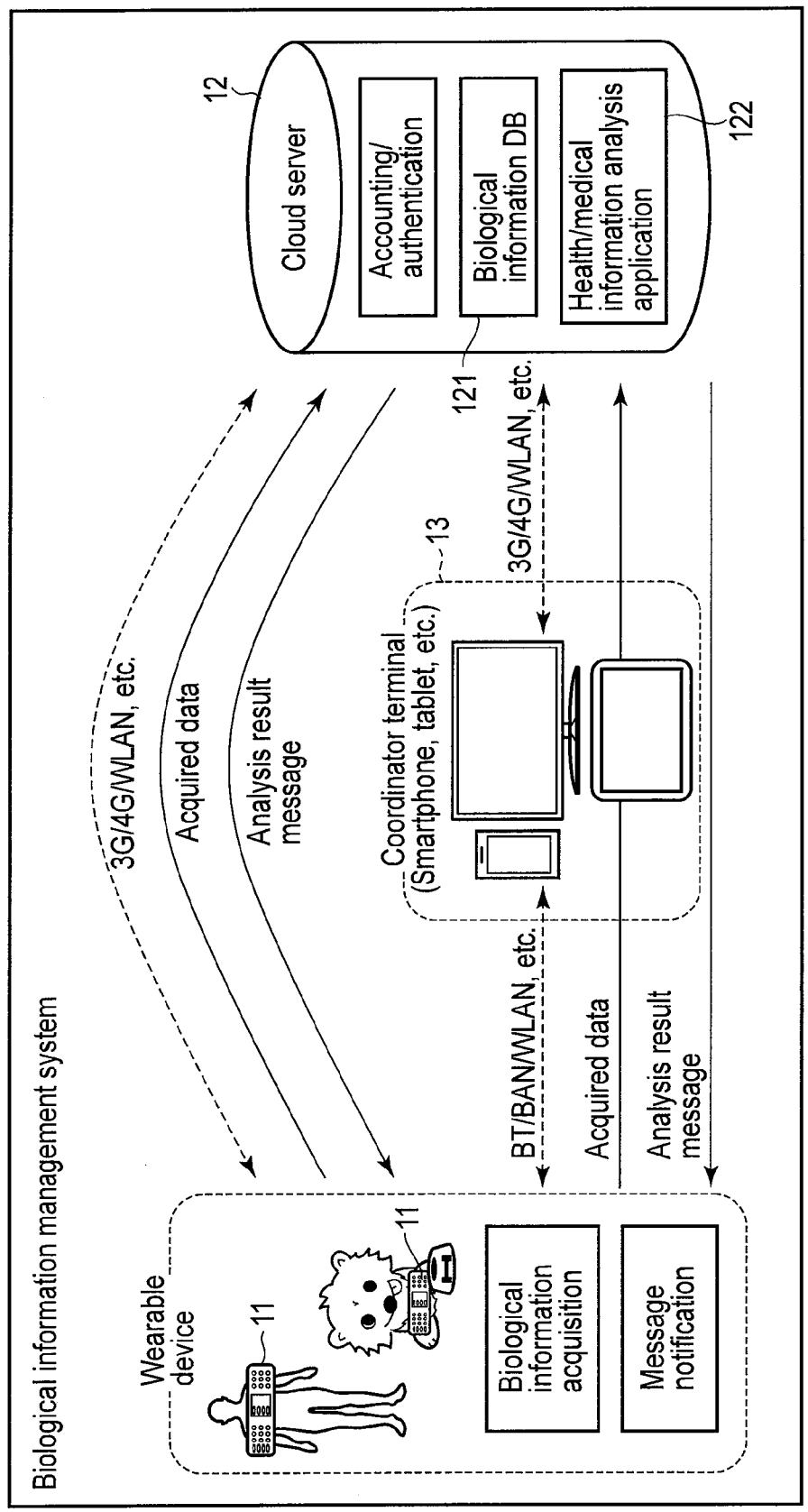
FIG. 1 is a view for describing an example of a biological information management system including an electronic apparatus according to an embodiment.

To begin with, referring to FIG. 1, a description is given of a biological information management system including an electronic apparatus according to an embodiment. The biological information management system includes a function of managing biological data of a user, which has been acquired by the electronic apparatus, and providing health information or medical information based on the biological data. This electronic apparatus is realized, for example, as a wearable device 11 which the user wears (puts on).

The wearable device 11 is realized as an embedded system built in various kinds of electronic apparatuses. The wearable device 11 has such a shape as to be wearable on a human body, for instance, the shape of a watch, glasses, a ring, a bracelet, a necklace, or a sticking plaster. Incidentally, the wearable device 11 can be attached to an animal as a collar. Accordingly, the biological information management system can also manage biological data of animals.

The wearable device 11 receives biological data relating to the pulse, cardiogram, body temperature, etc. by using a built-in biological sensor. Then, the wearable device 11 transmits the received biological data to one or more servers (cloud servers) 12. The wearable device 11 and a server of the one or more servers 12 establish connections based on various wireless communication schemes, such as 3G mobile communication, 4G mobile communication and wireless LAN (WLAN). Thereby, the wearable device 11 can transmit the biological data to the server 12.

In addition, the wearable device 11 can also transmit the biological data to the server 12 via a coordinator terminal (external electronic apparatus) 13 such as a smartphone, a tablet computer, or a television receiver. The wearable device 11 and the coordinator terminal 13 establish connections based on various wireless communication schemes, such as Bluetooth®, body area network (BAN) and wireless LAN. In addition, the coordinator terminal 13 and server 12 establish connections based on various wireless communication schemes, such as 3G mobile communication, 4G mobile communication and wireless LAN. Thereby, the biological data, which has been transmitted from the wearable device 11 to the coordinator terminal 13, can be transferred from the coordinator terminal 13 to the server 12.

The server 12 has a function of managing the wearable device 11 which is connected over the network. The server 12 authenticates the wearable device 11 (or the user of the wearable device 11) which requests a connection, and executes a process for accounting according to the provision of services. In addition, the server 12 receives biological data from the wearable device 11, and stores (accumulates) the received biological data in a biological information database 121 provided in the server 12.

A health/medical information application 122, which is executed on the server 12, analyzes the stored biological data, thereby notifying the wearable device 11 or the terminal of the administrator of a message (analysis result) for health support or medical information. The message is, for example, heat stroke information in a case where a rise in body temperature has been detected. The server 12 can also transmit the message to the wearable device 11 via the coordinator terminal 13.

By the message notified from the server 12, the user of the wearable device 11 can, for example, confirm his/her own health condition, or can obtain advice based on the health condition. Accordingly, before having a physical checkup or the like by a medical institution, the user can obtain brief information based on the stored biological data (biological features).

FIG. 2 is a view illustrating a system configuration of the wearable device 11. The wearable device 11 includes, for example, a system controller 101, a ROM 102, a RAM 103, a wireless communication module 104, a power controller 105, a battery 107, a storage device 108, a display device 109, and a biological sensor 110.

The system controller 101 controls the operations of the respective components in the wearable device 11. The system controller 101 includes a CPU 101A, and is connected to the ROM 102, RAM 103, wireless communication module 104, power controller 105, storage device 108, display device 109, and biological sensor 110.

The CPU 101A is a processor which loads instructions and data, which are stored in the ROM 102, into the RAM 103, and executes necessary processes. A communication control program 112 for controlling wireless communication is loaded in the RAM 103. The CPU 101A executes the communication control program 112 loaded in the RAM 103. The communication control program 112 includes a function of transmitting, with use of the wireless communication module 104, biological data, which has been generated by the biological sensor 110, to the server 12, and receiving a message notified from the server 12.

The biological sensor 110 includes one or more biological sensors 110A, 110B and 110C which detect signals occurring in the living body, such as signals of the pulse, cardiogram, body temperature, and blood pressure, and generate biological data based on the detected signals. The biological sensors 110A, 110B and 110C generate (output) so-called raw data as biological data relating to the pulse, cardiogram, body temperature, and blood pressure.

The wireless communication module 104 includes a plurality of wireless communication modules 104A, 104B and 104C for executing communications by a plurality of wireless communication schemes. The plural wireless communication schemes include various wireless communication schemes such as 3G mobile communication, 4G mobile communication, wireless LAN, Bluetooth, and BAN.

One of the plural wireless communication modules 104A, 104B and 104C transmits biological data, which has been generated by the biological sensor 110, and one or more biological features, which have been extracted (calculated) from the biological data, to the server 12. This wireless communication module can also transmit the biological data and biological features to the server 12 via the coordinator terminal 13. Moreover, the wireless communication module can receive a message based on the analysis result of the biological data or biological features from the server 12.

The display device 109 displays various types of information on the screen. The display device 109 displays on the screen, for instance, a message (health information, medical information) based on biological data, which is notified from the server 12.

The power controller 105 supplies power from the battery 107 to the respective components in the wearable device 11. In other words, the wearable device 11 is driven by the battery 107. The power controller 105 can also detect a battery level of the battery 107 (the remaining amount of the battery 107), the power consumption of the wearable device 11, etc.

As has been described above, any one of the wireless communication modules 104 provided in the wearable device 11 transmits to the server 12 the biological data generated by the biological sensor 110 and the biological features calculated from the biological data. In the communication path by the connection between the wireless communication module 104 and the server 12, it is possible that the communication condition varies due to various factors. For example, when the communication condition is good, the data (biological data or biological features) of a predetermined data amount can be transmitted to the server 12 in a short time. In short, communication can be executed with low power consumption when the communication condition is good. On the other hand, when the communication condition is not good, the time needed for transmitting the data of the predetermined data amount to the server 12 increases, and the power consumption needed for transmission increases.

Thus, in the present embodiment, the transmission/reception of data to/from the server 12 is controlled in accordance with the communication condition. For example, when the communication condition by the communication path between the wearable device 11 and the server 12 is good, the wearable device 11 transmits data of a large data amount, such as detailed biological data (raw data), to the server 12. When the communication condition is not good, the wearable device 11 transmits data of a small data amount, such as biological features calculated from the biological data, to the server 12. Thereby, power saving of the wearable device 11 can be achieved.

Figure 3:
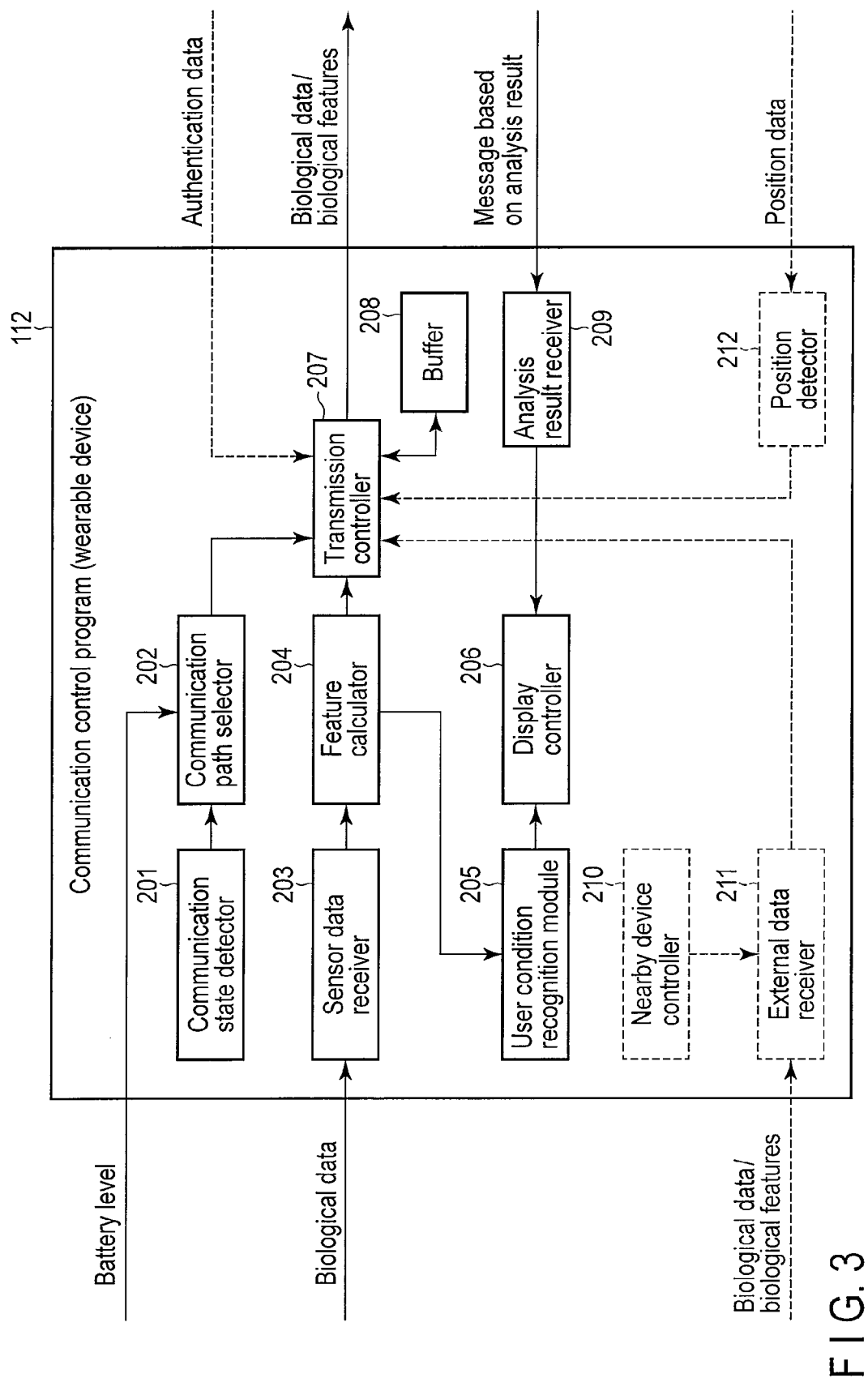
FIG. 3 is a block diagram illustrating an example of the functional configuration of a communication control program executed by the electronic apparatus of the embodiment.

FIG. 3 illustrates an example of the functional configuration of the communication control program 112 executed on the wearable device 11. The communication control program 112 includes, for example, a communication state detector 201, a communication path selector 202, a sensor data receiver 203, a feature calculator 204, a user condition recognition module 205, a display controller 206, a transmission controller 207, and an analysis result receiver 209.

The sensor data receiver 203 receives biological data which has been generated by the biological sensors 110. Each biological sensor 110, as described above, measures biological information of a user (e.g. pulse, blood pressure, cardiogram, body temperature) and then generates raw data including the measured biological information.

The feature calculator 204 extracts biological features from the received biological data. The feature calculator 204 calculates, for example, a heart rate (i.e. biological features) by analyzing the amplitude indicative of the pulse. Incidentally, the feature calculator 204 may be configured to improve the reliability of biological data by smoothing the biological data before calculating the biological features.

The user condition recognition module 205 recognizes the condition of the user by using the biological data or the biological features. The user condition recognition module 205 recognizes, for example, a sharp variation of biological information of the pulse or blood pressure.

When the user condition recognition module 205 has recognized a sharp variation of biological information, the display controller 206 may display a message (warning) on the screen of the display device 109. Incidentally, this message may be provided as a sound (alarm), with use of a speaker or an earphone.

In addition, the communication state detector 201 detects the communication state between the wireless communication module 104 of the own device 11 and the server 12. For example, the communication state detector 201 detects a plurality of communication states between the plural wireless communication modules 104A, 104B and 104C and the server 12 (the communication module of the server 12), which communicate by a plurality of communication schemes (e.g. 3G, 4G, wireless LAN). In other words, the communication state detector 201 detects the states of a plurality of communication paths between the plural wireless communication modules 104A, 104B and 104C and the server 12.

To be more specific, the communication state detector 201 detects the signal intensity of a signal received from the server (i.e. the intensity of a received radio wave), the response time in data transmission/reception, and the data transfer speed, with respect to each of the wireless communication modules 104A, 104B and 104C. Based on the detected signal intensity, response time and data transfer speed, the communication state detector 201 may calculate evaluation values of the communication states. The evaluation value indicates that the communication state is better as the value is greater.

Based on the communication states detected by the communication state detector 201, the communication path selector 202 selects a communication module for use in the communication with the server 12, from among the wireless communication modules 104A, 104B and 104C. Based on the detected communication states and the residual amount of the battery 107, the communication path selector 202 may select a communication module for use in the communication with the server 12, from among the wireless communication modules 104A, 104B and 104C. In other words, based on the communication states (or the communication states and residual battery amount), the communication path selector 202 selects a communication path for use in the communication with the server 12, from among communication paths by a plurality of communication schemes. In the meantime, the communication path selector 202 may select a communication module for use in the communication with the server 12, for example, by using evaluation values of the wireless communication modules 104A, 104B and 104C. The evaluation values of the wireless communication modules 104A, 104B and 104C are calculated, for example, based on the evaluation values of communication states, the residual battery amount, the power consumption and the data size of transmission-target data (e.g. evaluation values obtained by parametrizing these elements and adding the parameters with weighting).

With respect to each of the plural wireless communication modules 104A, 104B and 104C, the communication path selector 202 estimates, for example, the residual battery amount at a time when the transmission of target data is completed in the detected communication state. Then, the communication path selector 202 determines a communication module, with which the estimated residual battery amount at the time of completion of data transmission is a threshold or more, to be the communication module for use in the communication with the server 12. For example, the communication path selector 202 determines a communication module with which the estimated residual battery capacity is not emptied by data transmission to be the communication module for use in the communication with the server 12.

The transmission controller 207 controls the content of the data transmitted to the server 12, based on the communication state of the communication module that is used in the communication with the server 12. For example, based on the communication state of the communication module, the transmission controller 207 transmits to the server 12 at least either biological data or biological features calculated from the biological data.

To be more specific, when the communication state of the communication module for use in the communication with the server 12 is good (for example, when the evaluation value of the communication state is equal to or larger than a first threshold), the transmission controller 207 transmits the biological data to the server 12. When the communication state of the communication module is not good (i.e. poor) but the communication by the communication module is enabled, the transmission controller 207 transmits the biological features, which has smaller data size than the biological data, to the server 12. For example, when the evaluation value is smaller than the first threshold and is equal to or larger than a second threshold, the transmission controller 207 transmits the biological features to the server 12. In addition, when the communication by the communication module is disabled (for example, when the evaluation value is smaller than the second threshold), the transmission controller 207 accumulates (stores) the biological data and the biological features. When the communication becomes possible, the transmission controller 207 transmits the stored data (biological data or biological features) to the server 12. Thereby, in the wearable device 11, even when the communication state is not good, the power consumption needed for transmitting data to the server 12 can be suppressed. Incidentally, the transmission controller 207 may determine the frequency (time intervals) of data transmission, based on the communication state (e.g. signal intensity) by the communication module or the residual amount of the battery 107.

In addition, the communication state detector 201 and communication path selector 202 can also determine a communication module in a case of communicating with the server 12 via the coordinator terminal 13.

To be more specific, the communication state detector 201 detects, for example, the communication states of the communication modules (e.g. communication paths by BT, BAN and wireless LAN) which can be used for the communication between the own device 11 and the coordinator terminal 13. Then, based on the detected communication states and the residual amount of the battery 107, the communication path selector 202 determines the communication module used for the communication between the own device 11 and the coordinator terminal 13. In the meantime, the coordinator terminal 13 and server 12 may select communication modules, which are respectively used by the coordinator terminal 13 and server 12, by similar methods.

The transmission controller 207 controls the content of the data which is transmitted to the server 12 via the coordinator terminal 13, based on the communication state of the communication module which has been determined. For example, based on the communication state of the communication module, the transmission controller 207 transmits at least one of biological data and biological features, which have been calculated from the biological data, to the server 12 via the coordinator terminal 13.

To be more specific, when the communication state of the communication module for use in the communication with the coordinator terminal 13 is good, the transmission controller 207 transmits both the biological data and the biological features to the server 12 via the coordinator terminal 13. For example, when the evaluation value of the communication state is equal to or larger than a first threshold, the transmission controller 207 transmits both the biological data and the biological features to the server 12. When the communication state of the communication module is not good but the communication by the communication module is enabled, the transmission controller 207 transmits the biological features, which have been calculated by the feature calculator 204, to the server 12 via the coordinator terminal 13. For example, when the evaluation value is smaller than the first threshold and is equal to or larger than a second threshold, the transmission controller 207 transmits the biological features to the server 12. In addition, when the communication by the communication module is disabled, the transmission controller 207 stores the biological data and the biological features in a buffer 208 and, when the communication is enabled, transmits the stored data (biological data and/or biological features) to the server 12 via the coordinator terminal 13. For example, when the evaluation value is smaller than the second threshold, the transmission controller 207 stores the biological data and the biological features in a buffer 208.

The server 12 receives at least one of the biological data and biological features which are transmitted from the wearable device 11, and stores at least one of the biological data and biological features in the biological information database 121. The health/medical information application 122, which is executed on the server 12, analyzes at least one of the stored biological data and biological features, generates a message of health support or medical information, based on the analysis result, and transmits (notifies) the message to the wearable device 11.

The analysis result receiver 209 receives the message based on at least one of the biological data and biological features from the server 12, by using the communication module selected by the communication path selector 202. This message is a message based on the analysis result of the biological data or biological features and is, for example, heat stroke information in a case where the rise in body temperature has been detected. The analysis result receiver 209 may receive the message from the server 12 via the coordinator terminal 13.

The display controller 206 displays the received message on the screen of the display device 109. By viewing the displayed message, the user can confirm his or her health condition, or can obtain advice based on the health condition. Incidentally, this message may be provided as audio information, with use of a speaker or an earphone.

By the above-described structure, since the biological information obtained by the wearable device 11 can be efficiently transmitted to the server 12, power saving of the wearable device 11 can be achieved.

Next, FIG. 4 illustrates an example in which when there are a plurality of wearable devices, biological information is transmitted from the wearable devices to the server 12. In the example shown in FIG. 4, it is assumed that a plurality of wearable devices 11A, 11B, 11C and 11D having different performances are present nearby. The performance is indicated by, for example, various information items (parameters) relating to the wearable device, such as the processing speed of the processor, the size (buffer size) of the memory, the power consumption, the residual battery amount, the wireless communication scheme usable in the wireless communication module, and the signal intensity.

In each of the wearable devices 11A, 11B, 11C and 11D, the time (available time) during which battery-powered use is enabled is estimated. The available time varies depending on which of the wireless communication schemes (wireless communication modules) is used by the wearable device 11 to execute communication. In general, the power consumption in a case where the wearable device executes communication by wireless LAN, 3G mobile communication or 4G mobile communication is greater than the power consumption in a case where the wearable device executes communication by BT or BAN for communication over a shorter distance than the wireless LAN, 3G mobile communication or 4G mobile communication. In other words, when communication is executed by BT or BAN, the available time of the wearable device 11 can be made longer than in the case where communication is executed by wireless LAN, 3G mobile communication or 4G mobile communication.

In the wearable device 11B, 11C with a short available time (e.g. a wearable device with an available time of less than a first threshold time), it is desirable to increase the available time as much as possible by executing communication by BT or BAN with low power consumption. Thus, the wearable device 11A with a long available time (e.g. wearable device 11A with an available time of a second threshold time (>first threshold time) or more) establishes a connection by BT or BAN to the wearable device 11B, 11C (external electronic apparatus) with a short available time. Then, the wearable device 11A receives biological data and biological features calculated from the biological data from the wearable device 11B, 11C. The wearable device 11A also establishes a connection to the server 12 by wireless LAN, 3G mobile communication or 4G mobile communication. Based on the communication state in this connection, the wearable device 11A transmits to the server 12 at least either the biological data generated by the own device 11A and biological data received from the wearable device 11B, 11C, or the biological features calculated by the own device 11A and biological features received from the wearable device 11B, 11C. Specifically, the wearable device 11A with the long available time transmits to the server 12 the data of the own device 11A together with the data of the wearable device 11B, 11C with the short available time.

The wearable device 11A may establish a connection to the coordinator terminal 13 by BT, BAN or wireless LAN, thereby transmitting the biological data (or biological features) generated by the own device 11A and the biological data (or biological features) received from the wearable device 11B, 11C to the coordinator terminal 13. In this case, the coordinator terminal 13 establishes a connection to the server 12 by wireless LAN, 3G mobile communication or 4G mobile communication. Then, the coordinator terminal 13 transmits to the server 12 the biological data (or biological features) generated by the own device 11A and biological data (or biological features) generated by the wearable device 11A, 11B, 11C, which have been received from the wearable device 11A.

The wearable device 11D with an intermediate available time (e.g. a wearable device with an available time of the first threshold time or more and less than the second threshold time) transmits biological data to the server 12 by wireless LAN, 3G mobile communication or 4G mobile communication, as in the example shown in FIG. 1. In addition, the wearable device 11D may transmit the biological data to the server 12 via the coordinator terminal 13 which is connected by BT, BAN or wireless LAN.

As regards this data transmission, the operation of the communication control program 112, which is executed on the wearable device 11A, will be described.

A nearby device controller 210, which is provided in the communication control program 112, detects other wearable devices 11B, 11C and 11D which are present near the wearable device (own device) 11A. Then, the nearby device controller 210 determines a device (server connection device) which is to be directly connected to the server 12, from among the own device 11A and the detected nearby wearable devices 11B, 11C and 11D.

In the example shown in FIG. 4, the nearby device controller 210 determines, for example, the own device 11A with a longest available time (highest performance) to be the server connection device, based on the available time (performance) of the own device 11A and the available time (performance) of each of the nearby wearable devices 11B, 11C and 11D. In addition, the nearby device controller 210 determines the wearable device 11B, 11C with a short available time to be a device (non-server-connection device) indirectly connected to the server 12. Specifically, the nearby device controller 210 determines that the own device 11A, which is the server connection device, relays the data, which is transmitted from/to the wearable device 11B, 11C with the short available time. Furthermore, the nearby device controller 210 determines that the wearable device 11D with the intermediate available time transmits data to the server 12 and receives data from the server 12 by the own device 11D.

In the meantime, the nearby device controller 210 may determine the server connection device, etc., based on not only the available time, but also an evaluation value calculated (e.g. weighted addition) by weighting parameters indicative of the residual battery amount, signal intensity, etc. In addition, the nearby device controller 210 can also determine that the own device 11A and the wearable device 11D communicate with the server 12 via the coordinator terminal 13.

Subsequently, an external data receiver 211 receives biological data from the wearable device 11B, 11C (non-server-connection device). Incidentally, the external data receiver 211 may receive the biological data and the biological features calculated with use of the biological data, from the wearable device 11B, 11C. In addition, the external data receiver 211 may receive the biological data from the wearable device 11B, 11C, and then the feature calculator 204 may calculate the biological features from the received biological data.

Based on the communication states detected by the communication state detector 201 and the residual battery amount, the communication path selector 202 selects a communication module for transferring data from the own device 11A to the server 12, from among a plurality of communication modules.

The transmission controller 207 controls the content of the data transmitted to the server 12, based on the communication state of the communication module that has been selected by the communication path selector 202. For example, when the communication state of the selected communication module is good, the transmission controller 207 transmits to the server 12 the biological data of the own device 11A and the biological data which has been received from the wearable device 11B, 11C. For example, when the evaluation value of the communication state is equal to or larger than a first threshold, the transmission controller 207 transmits to the server 12 the biological data of the own device 11A and the biological data of the wearable device 11B, 11C. When the communication state of the selected communication module is not good but the communication by the communication module is enabled, the transmission controller 207 transmits to the server 12 the biological features of the own device 11A, which have been calculated by the feature calculator 204, and the biological features received from the wearable device 11B, 11C. For example, when the evaluation value is smaller than the first threshold and is equal to or larger than a second threshold, the transmission controller 207 transmits to the server 12 the biological features of the own device 11A and the biological features received of the wearable device 11B, 11C. In addition, when the communication by the selected communication module is disabled (for example, when the evaluation value is less than the second threshold), the transmission controller 207 accumulates (stores) in the buffer 208 the biological data and biological features of the own device 11A and the biological data and biological features received from the wearable device 11B, 11C. When the communication then becomes possible, the transmission controller 207 transmits the stored data (biological data or biological features) to the server 12.

By the above-described structure, when a plurality of wearable devices are present nearby, the transmission of data from such plural wearable devices to the server 12 can be optimized in consideration of the communication state and available time (performance).

The above-described example relates to the case in which biological data is transmitted from the wearable device 11 to the server 12. However, the embodiment is also applicable to the case of transmitting a message based on an analysis result of biological data from the server 12 to the wearable device 11. Specifically, the wearable device 11A with the long available time establishes a connection to the server 12 by wireless LAN, 3G mobile communication or 4G mobile communication, and receives messages (messages based on the analysis of biological data of each wearable device 11) for the own device 11A and the wearable device 11B, 11C with the short available time. Then, the wearable device 11A establishes a connection to the wearable device 11B, 11C by BT or BAN, and transmits the messages, which have been received from the server 12, to the wearable device 11B, 11C.

Furthermore, as illustrated in FIG. 5, the content of biological data, which is transmitted to the server 12, or the transmission frequency of biological data, may be altered in accordance with the location (position) where the wearable device 11 is used.

A position detector 212 detects the position of the wearable device (own device) 11. For example, when the server 12 authenticates the wearable device 11, the position detector 212 receives position data based on the server 12, or a path (e.g. IP address) on the network that is used for connection to the server 12, and detects the position of the own device 11 by using this position data. In addition, the position detector 212 may detect the present position of the own device 11 by using a signal received by a GPS receiver in the wearable device 11.

Then, the position detector 212 recognizes a location (e.g. a place name, a facility name) corresponding to the position of the own device 11. In addition, the position detector 212 may recognize the attribute of the location corresponding to the position of the own device 11. This attribute may be indicative of, for instance, the type of place, such as a hospital, a company, an event site, or one's own home, or may be indicative of the transmission frequency of data to the server 12 and the content of data that is transmitted.

The transmission controller 207 determines the transmission frequency of data to the server 12 and the content of data that is transmitted, based on the location where the own device 11 is used, or the attribute of the location. For example, when the own device 11 is located within a hospital, the transmission controller 207 transmits detailed biological data to the server 12 with a high frequency. In addition, for example, when the own device 11 is located within a company or an event site, the transmission controller 207 transmits simple data, such as biological features, which have been generated (extracted) from biological data, to the server 12.

By the above-described structure, necessary biological information can be transmitted to the server 12, in accordance with the location (attribute of location) where the wearable device 11 is used. For example, when accurate biological data or real-time biological data is required, such as when the user is hospitalized, the interval of transmission of biological data is shortened, and raw data, which has been output by the biological sensor, is transmitted to the server 12 as such. In addition, for example, when there are many persons wearing wearable devices 11, as in a company or an event, the amount of data is reduced by converting the biological data to biological feature data, and the transmission interval of the biological feature data is made longer. In this manner, the data transmission method is controlled in accordance with the position (location), whereby the convergence in data transmission can be reduced and the reliability, etc. of data transfer can adaptively be controlled.

In the meantime, the communication path selector 202 may select the wireless communication module 104 for use in the communication with the server 12, from among plural wireless communication modules 104, in accordance with the location where the own device 11 is used. For example, when the own device 11 is used in a location where wireless LAN is available (e.g. a hospital, or one's own home), the communication path selector 202 preferentially selects the wireless communication module 104 of wireless LAN. For such selection, priority may be given in advance to the respective wireless communication modules 104 (communication paths) in association with the location where the wearable device 11 is used.

Next, referring to a flowchart of FIG. 6, a description is given of an example of the procedure of a data transmission process executed by the wearable device 11.

To begin with, the biological sensors 110 start measuring the user's biological information (e.g. the pulse, blood pressure, cardiogram, and body temperature) (block B101). The biological sensors 110 generate biological data (sensor data) including the measured biological information. The sensor data receiver 203 acquires (receives) the biological data which has been generated by the biological sensors 110 (block B102).

The feature calculator 204 calculates (extracts) biological features by using the received biological data (block B103). The feature calculator 204 calculates, for example, a heart rate (biological features) by analyzing the amplitude indicative of the pulse. The user condition recognition module 205 recognizes the condition of the user by using the biological data or the biological features (block B104). The display controller 206 may display a message or the like on the screen of the wearable device 11, based on the recognized condition of the user.

Next, the communication state detector 201 detects the states of communication paths for transferring data to the server 12 (the states of communication by the communication modules 104) (block B105). For example, the communication state detector 201 calculates the evaluation value of the communication state, based on the signal intensity, response time and transmission speed. The evaluation value indicates that the communication state is better as the value is greater. Based on the communication states detected by the communication state detector 201 and the residual battery amount, the communication path selector 202 selects, from among a plurality of communication paths, a communication path for transferring data to the server 12 (block B106).

Then, the transmission controller 207 determines whether the communication state of the selected communication path is good or not (block B107). For example, the transmission controller 207 determines whether the evaluation value indicative of the communication state is equal to or larger than a threshold. If the communication state is good (for example, if the evaluation value is equal to or larger than the threshold) (YES in block B107), the transmission controller 207 transmits the biological data to the server 12 (block B108).

When the communication state is not good (e.g. when the evaluation value is smaller than the threshold value) (NO in block B107), the transmission controller 207 determines whether communication is enabled by the selected communication path (block B109). If communication is enabled (YES in block B109), the transmission controller 207 transmits the biological features, which have been calculated from the biological data, to the server 12 (block B110). When communication is disabled (NO in block B109), the transmission controller 207 stores the biological data and the biological features in the buffer 208 (block B111) and, when the communication is enabled, transmits the stored data (biological data or biological features) to the server 12.

Subsequently, the biological sensor 110 determines whether or not to end the measurement (block B112). For example, the biological sensor 110 determines whether the user has instructed the end of the measurement. When the measurement is not ended (NO in block B112), the process returns to block B102, and the process relating to the acquisition and transfer of sensor data is continued. When the measurement is ended (YES in block B112), the process is terminated.

Figure 7:
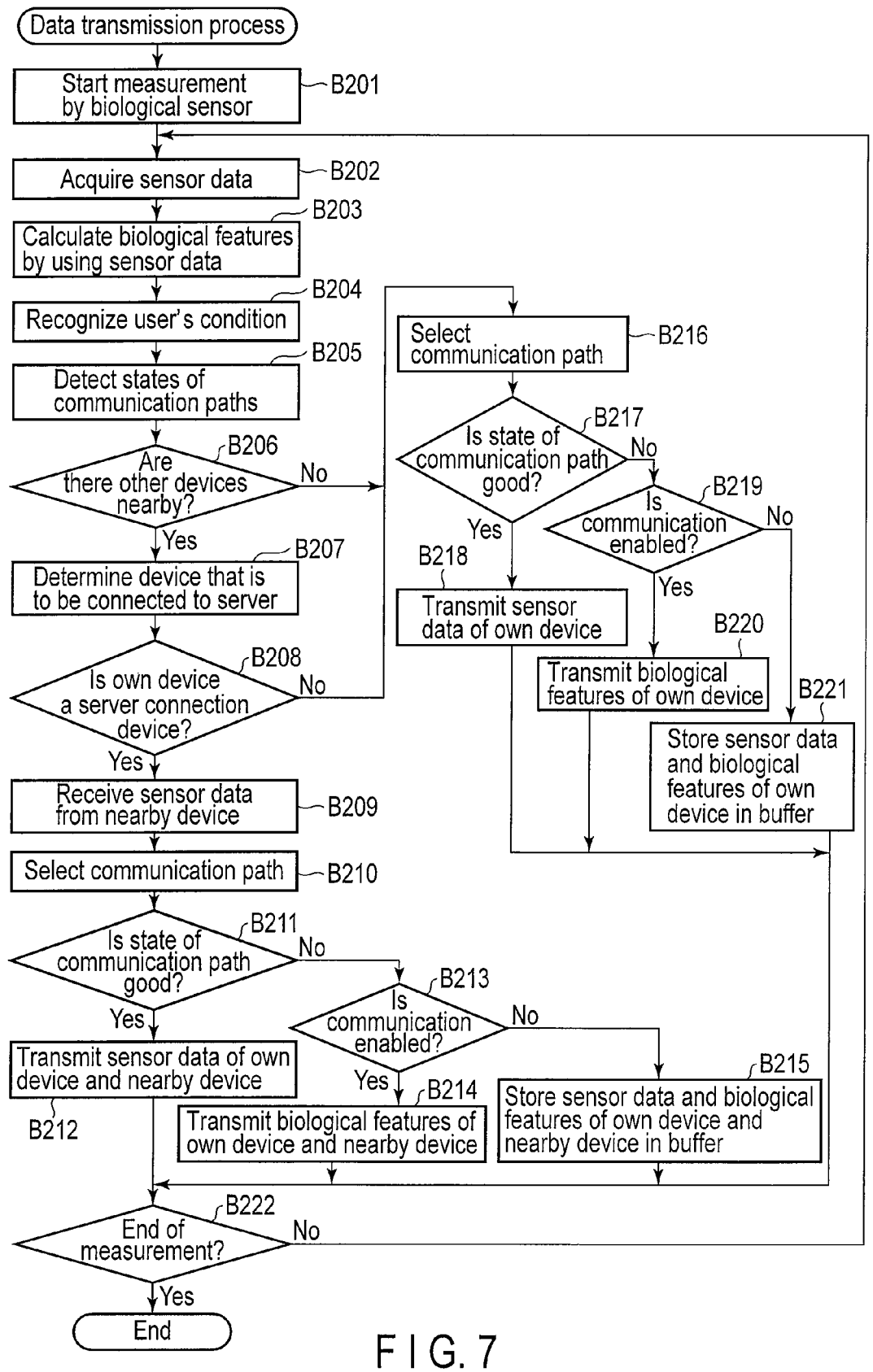
FIG. 7 is a flowchart illustrating another example of the procedure of the data transmission process executed by the electronic apparatus of the embodiment.

In addition, referring to a flowchart of FIG. 7, a description is given of another example of the procedure of the data transmission process executed by the wearable device 11. In this data transmission process, it is assumed that the wearable device 11 has a function of controlling data transmission from the own device 11 to the server 12 and controlling data transmission to the server 12 via nearby wearable devices when there are other wearable devices near the wearable device 11.

The procedure from block B201 to block B205 is the same as the procedure from block B101 to block B105 which have been described with reference to the flowchart of FIG. 6.

The nearby device controller 210 determines whether there are other wearable devices near the wearable device (own device) 11 (block B206). When there are other wearable devices near the own device 11 (YES in block B206), the nearby device controller 210 detects wearable devices near the own device 11, and determines a device (server connection device) which is to be connected to the server 12, from among the own device 11 and the detected nearby devices (block B207). The nearby device controller 210 adaptively determines the server connection device, based on the performance and residual battery amount of the own device 11, the performance and residual battery amount of each of the nearby wearable devices, and the communication state. For example, the nearby device controller 210 determines a wearable device with a highest performance to be the server connection device.

Then, the nearby device controller 210 determines whether the own device 11 is the server connection device or not (block B208). When the own device 11 is the server connection device (YES in block B208), the external data receiver 211 receives biological data from the nearby wearable device (block B209). The nearby wearable device transmits the biological data to the server connection device 11 in accordance with the communication state. Incidentally, the external data receiver 211 may receive the biological data and the biological features calculated with use of the biological data, from the nearby wearable device. Then, based on the communication states detected by the communication state detector 201 and the residual battery amount, the communication path selector 202 selects a communication path for transferring data to the server 12, from among a plurality of communication paths (block B210).

Subsequently, the transmission controller 207 determines whether the communication state of the selected communication path is good or not (block B211). If the communication state is good (for example, if the evaluation value is equal to or larger than the threshold) (YES in block B211), the transmission controller 207 transmits the biological data of the own device 11 and the biological data of the nearby wearable device to the server 12 (block B212).

When the communication state is not good (for example, when the evaluation value is smaller than the threshold) (NO in block B211), the transmission controller 207 determines whether communication is enabled by the selected communication path (block B213). If communication is enabled (YES in block B213), the transmission controller 207 transmits to the server 12 the biological features, which have been calculated from the biological data of the own device 11, and the biological features, which have been calculated from the biological data of the nearby wearable device (block B214). When communication is disabled (NO in block B213), the transmission controller 207 stores the biological data and biological features of the own device 11 and the biological data and biological features of the nearby wearable device in the buffer 208 (block B215). The transmission controller 207 transmits the stored data (biological data or biological features) to the server 12 when the communication is enabled.

On the other hand, when there are no other wearable devices near the own device 11 (NO in block B206), the communication path selector 202 selects, from among communication paths, a communication path for transferring data to the server 12, based on the communication states detected by the communication state detector 201 and the residual battery amount (block B216).

In addition, when the own device 11 is not the server connection device (NO in block B208), the communication path selector 202 selects a communication path for transferring data to the wearable device which has been selected as the server connection device (block B216). In the meantime, the communication path selector 202 may cause the communication state detector 201 to detect the communication state between the own device 11 and the server connection device, and may select a communication path, based on the detected communication state.

After the communication path to the server 12 or the server connection device has been selected in block B216, the transmission controller 207 determines whether the communication state of the selected communication path is good or not (block B217). If the communication state is good (for example, if the evaluation value is equal to or larger than the threshold) (YES in block B217), the transmission controller 207 transmits the biological data of the own device 11 to the server 12 or the server connection device (block B218).

When the communication state is not good (for example, when the evaluation value is smaller than the threshold) (NO in block B217), the transmission controller 207 determines whether communication is enabled by the selected communication path (block B219). If communication is enabled (YES in block B219), the transmission controller 207 transmits the biological features, which have been calculated from the biological data, to the server 12 or the server connection device (block B220). When communication is disabled (NO in block B219), the transmission controller 207 stores the biological data and biological features of the own device 11 in the buffer 208 (block B221) and, when the communication is enabled, transmits the stored data (biological data or biological features) to the server 12 or the server connection device.

Subsequently, the biological sensor 110 determines whether or not to end the measurement (block B222). For example, the biological sensor 110 determines whether the user has instructed the end of the measurement. When the measurement is not ended (NO in block B222), the process returns to block B202, and the process relating to the acquisition and transfer of sensor data is continued. When the measurement is ended (YES in block B222), the process is terminated.

Besides, referring to a flowchart of FIG. 8, a description is given of still another example of the procedure of the data transmission process executed by the wearable device 11. In this data transmission process, it is assumed that the wearable device 11 has a function of controlling the content of the data, which is to be transmitted, in accordance with the position (location) where the wearable device 11 is used.

The procedure from block B301 to block B304 is the same as the procedure from block B101 to block B104 which have been described with reference to the flowchart of FIG. 6.

The position detector 212 detects the position of the wearable device (own device) 11 (block B305). For example, when the server 12 authenticates the wearable device 11, the position detector 212 receives position data based on the server 12, or a path (e.g. IP address) on the network that is used for connection to the server 12, and detects the position of the own device 11 by using this position data.

The transmission controller 207 determines whether the own device 11 is present within a predetermined area or not (block B306). This predetermined area is an area where high-accuracy biological data needs to be acquired with a high frequency (at short transmission intervals), for example, as in a hospital.

When the own device 11 is within the predetermined area (YES in block B306), the transmission controller 207 transmits the biological data to the server 12 (block B307). On the other hand, when the own device 11 is not within the predetermined area (NO in block B306), the transmission controller 207 transmits the biological features, which have been calculated from the biological data, to the server 12 (block B308). In the meantime, when the own device 11 is not within the predetermined area, the transmission controller 207 may make longer the transmission interval of the biological features.

Subsequently, the biological sensor 110 determines whether or not to end the measurement (block B309). For example, the biological sensor 110 determines whether the user has instructed the end of the measurement. When the measurement is not ended (NO in block B309), the process returns to block B302, and the process relating to the acquisition and transfer of sensor data is continued. When the measurement is ended (YES in block B309), the process is terminated.

The above-described procedure based on the position of the wearable device 11 can be used by incorporating the procedures illustrated in FIGS. 6 and 7.

As has been described above, according to the present embodiment, biological information can efficiently be transferred. The biological sensor 110 generates biological data. The feature calculator 204 calculates the biological features from the biological data. The communication state detector 201 detects the communication state between the wireless communication module 104A, 104B, 104C and the server 12. Based on the detected communication state, the transmission controller 207 transmits at least one of the biological data and the biological features to the server 12.

In this manner, since at least one of the biological data and the biological features are transmitted in accordance with the communication state, it is possible to efficiently transmit biological information and realize a health care system with low power consumption and high reliability.

All the procedures of the data transmission process of the present embodiment can be executed by software. Thus, the same advantageous effects as with the present embodiment can easily be obtained simply by installing a computer program, which executes the procedures of the data transmission process, into an ordinary computer through a computer-readable storage medium which stores the computer program, and by executing the computer program.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic apparatus comprising:
a biological sensor configured to generate first biological data;
at least one processor configured to: extract one or more first features from the first biological data;
detect a communication state between a communication device and a server; and
calculate an evaluation value of the communication state; and
a transmission controller configured to transmit at least one of the first biological data and the one or more first features to the server, based on the detected communication state,
wherein the transmission controller is configured to transmit the first biological data to the server when the evaluation value is equal to or larger than a first threshold, to transmit the one or more first features to the server when the evaluation value is smaller than the first threshold and is equal to or larger than a second threshold, and to store the first biological data and the one or more first features in a buffer when the evaluation value is smaller than the second threshold.

2. The electronic apparatus of claim 1, further comprising the communication device.

3. The electronic apparatus of claim 1, further comprising:
a receiver configured to receive a message from the server, the message being generated based on at least one of the first biological data and the one or more first features; and
a display controller configured to display the message on a screen.

4. The electronic apparatus of claim 1, further comprising a receiver configured to receive second biological data and one or more second features from an external electronic apparatus, the one or more second features being extracted from the second biological data,
wherein the transmission controller is configured to transmit at least either the first biological data and the second biological data or the one or more first features and the one or more second features to the server, based on the communication state.

5. The electronic apparatus of claim 1, wherein the at least one processor is further configured to detect a location where the electronic apparatus is used,
wherein the transmission controller is configured to transmit the first biological data to the server when the detected location is a first location, and to transmit the one or more first features to the server when the detected location is not the first location.

6. The electronic apparatus of claim 1, wherein the at least one processor is further configured to: detect a plurality of communication states between a plurality of communication devices and the server, the plurality of communication devices communicating by a plurality of communication schemes; and
select a first communication device of the plurality of communication devices, based on the plurality of communication states, and
the transmission controller is configured to transmit at least one of the first biological data and the one or more first features to the server, based on the communication state of the first communication device.

7. The electronic apparatus of claim 6, wherein the at least one processor is further configured to select the first communication device based on the plurality of communication states and a battery level.

8. The electronic apparatus of claim 1, wherein the at least one processor is further configured to detect a communication state between the communication device and an external electronic apparatus, and
the transmission controller is configured to transmit at least one of the first biological data and the one or more first features to the server via the external electronic apparatus, based on the communication state between the communication device and the external electronic apparatus.

9. The electronic apparatus of claim 8, further comprising:
a receiver configured to receive a message from the server via the external electronic apparatus, the message being generated based on at least one of the first biological data and the one or more first features; and
a display controller configured to display the message on a screen.

10. A communication control method comprising:
sensing first biological data;
extracting one or more first features from the first biological data;
detecting a communication state between a communication device and a server;
calculating an evaluation value of the communication state; and
transmitting at least one of the first biological data and the one or more first features to the server, based on the detected communication state,
wherein the transmitting comprising transmitting the first biological data to the server when the evaluation value is equal to or larger than a first threshold, transmitting the one or more first features to the server when the evaluation value is smaller than the first threshold and is equal to or larger than a second threshold and storing the first biological data and the one or more first features in a buffer when the evaluation value is smaller than the second threshold.

11. A biological data management system comprising a wearable device and a server, the wearable device comprising:
- a biological sensor configured to generate first biological data;
- at least one processor configured to: extract one or more first features from the first biological data;
- detect a communication state between a communication device and a server; and
- calculate an evaluation value of the communication state; and
- a transmission controller configured to transmit at least one of the first biological data and the one or more first features to the server, based on the detected communication state, and
- wherein the server comprises a storage processor configured to store in a storage device at least one of the first biological data and the one or more first features transmitted from the wearable device,
- wherein the transmission controller is configured to transmit the first biological data to the server when the evaluation value is equal to or larger than a first threshold, to transmit the one or more first features to the server when the evaluation value is smaller than the first threshold and is equal to or larger than a second threshold, and to store the first biological data and the one or more first features in a buffer when the evaluation value is smaller than the second threshold.

* * * * *